(12) United States Patent
Chen et al.

(10) Patent No.: US 12,064,090 B2
(45) Date of Patent: Aug. 20, 2024

(54) ENDOSCOPE TIP ASSEMBLY USING CAVITY INTERPOSER TO ALLOW COPLANAR CAMERA AND LEDs

(71) Applicant: OmniVision Technologies, Inc., Santa Clara, CA (US)

(72) Inventors: Teng-Sheng Chen, Hsinchu (TW); Wei-Ping Chen, New Taipei (TW); Jau-Jan Deng, Taipei (TW); Wei-Feng Lin, Hsinchu (TW); Chun-Sheng Fan, Zhudong Township (TW)

(73) Assignee: OmniVision Technologies, Inc., Santa Clara, CA (US)

( * ) Notice: Subject to any disclaimer, the term of this patent is extended or adjusted under 35 U.S.C. 154(b) by 0 days.

(21) Appl. No.: 17/504,105

(22) Filed: Oct. 18, 2021

(65) Prior Publication Data

US 2023/0122722 A1    Apr. 20, 2023

(51) Int. Cl.
*A61B 1/00* (2006.01)
*A61B 1/05* (2006.01)
*A61B 1/06* (2006.01)

(52) U.S. Cl.
CPC .......... *A61B 1/051* (2013.01); *A61B 1/00096* (2013.01); *A61B 1/0638* (2013.01); *A61B 1/0684* (2013.01)

(58) Field of Classification Search
CPC ... A61B 1/0008; A61B 1/00186; A61B 1/051; A61B 1/0638; A61B 1/0684; A61B 1/043; A61B 1/046; A61B 1/0646
See application file for complete search history.

(56) References Cited

U.S. PATENT DOCUMENTS

| 9,538,909 B2 | 1/2017 | Lei et al. |
| 9,913,573 B2 | 3/2018 | Banik et al. |
| 10,924,640 B2 | 2/2021 | Shimohata |

(Continued)

FOREIGN PATENT DOCUMENTS

| EP | 1839559 B1 | 9/2015 |
| EP | 2687144 B1 | 11/2017 |
| WO | WO 2018/136950 A1 | 7/2018 |

OTHER PUBLICATIONS

U.S. Appl. No. 17/674,675 Office Action dated Mar. 2, 2023, 20 pages.

(Continued)

*Primary Examiner* — Timothy J Neal
(74) *Attorney, Agent, or Firm* — COZEN O'CONNOR

(57) ABSTRACT

A cavity interposer has a cavity, first bondpads adapted to couple to a chip-type camera cube disposed within a base of the cavity at a first level, the first bondpads coupled through feedthroughs to second bondpads at a base of the interposer at a second level; and third bondpads adapted to couple to a light-emitting diode (LED), the third bondpads at a third level. The third bondpads coupled to fourth bondpads at the base of the interposer at the second level; and the second and fourth bondpads couple to conductors of a cable with the first, second, and third level different. An endoscope optical includes the cavity interposer an LED, and a chip-type camera cube electrically bonded to the first bondpads; the LED is bonded to the third bondpads; and a top of the chip-type camera cube and a top of the LED are at a same level.

18 Claims, 3 Drawing Sheets

(56) References Cited

U.S. PATENT DOCUMENTS

| | | | |
|---|---|---|---|
| 11,147,437 B1 | 10/2021 | Ochi et al. | |
| 11,172,806 B2 | 11/2021 | Chen et al. | |
| 2003/0220574 A1* | 11/2003 | Markus | A61B 1/05 600/466 |
| 2004/0038447 A1 | 2/2004 | Corisis | |
| 2004/0233319 A1 | 11/2004 | You et al. | |
| 2005/0143623 A1 | 6/2005 | Kojima | |
| 2005/0174473 A1 | 8/2005 | Morgan et al. | |
| 2005/0236708 A1 | 10/2005 | Farnworth et al. | |
| 2005/0267328 A1* | 12/2005 | Blumzvig | G02B 13/0065 348/E5.029 |
| 2005/0275748 A1 | 12/2005 | Takekuma et al. | |
| 2007/0206114 A1 | 9/2007 | Tanaka et al. | |
| 2008/0255416 A1* | 10/2008 | Gilboa | A61B 1/055 600/110 |
| 2009/0153729 A1 | 6/2009 | Hiltunen et al. | |
| 2012/0148225 A1 | 6/2012 | Chow et al. | |
| 2013/0258182 A1 | 10/2013 | Lin et al. | |
| 2014/0098208 A1* | 4/2014 | Makino | A61B 1/041 348/76 |
| 2016/0112622 A1 | 4/2016 | Gressum | |
| 2017/0310890 A1 | 10/2017 | Wan et al. | |
| 2018/0070806 A1* | 3/2018 | Matsuo | A61B 1/043 |
| 2019/0089875 A1* | 3/2019 | Fan | A61B 1/051 |
| 2019/0246884 A1 | 8/2019 | Lu | |
| 2020/0274995 A1 | 8/2020 | Coleman | |
| 2021/0037169 A1* | 2/2021 | Numasawa | A61B 1/06 |
| 2021/0217795 A1 | 7/2021 | Takada et al. | |
| 2021/0242099 A1* | 8/2021 | Takeshita | H01L 23/13 |
| 2021/0249393 A1* | 8/2021 | Wu | H05K 1/189 |

OTHER PUBLICATIONS

U.S. Appl. No. 17/674,675 Final Office Action dated Sep. 14, 2023, 25 pages.

\* cited by examiner

ENDOSCOPE TIP ASSEMBLY USING CAVITY INTERPOSER TO ALLOW COPLANAR CAMERA AND LEDs

BACKGROUND

Endoscopes have become common in Medicine to inspect tissues or observe and direct surgery without having to make large incisions so the unaided eye can see those tissues, and similar devices are often used for inspection in tight places of mechanical devices to avoid requiring disassembly. Typically, a distal end of the endoscope is inserted into the tight places or into the body, and a physician or other user observes images displayed through display apparatus near a proximal end of the endoscope.

Past endoscopes often had cameras with lenses that focused light onto an end of a coherent optical fiber bundle at the distal end of the endoscope, and directed light through an optical fiber from an external illuminator onto tissue or parts to be inspected located in front of the lenses; the optical fiber brought images from the distal end of the endoscope to display apparatus near the proximal end of the endoscope.

As electronic cameras have become smaller, there is an increasing trend towards placing light sources, such as light emitting diodes (LEDs) or laser diodes, and electronic cameras, at the distal end of the endoscope and transmitting signals from the electronic cameras to the display apparatus near the proximal end of the endoscope.

Chip-type electronic cameras have become common in cell phones and similar devices. They are formed at wafer level by bonding a wafer of image sensor integrated circuits to a spacer wafer, and bonding to the spacer wafer a wafer of lenses, such that a lens is positioned in front of and spaced at a focal length from, each image sensor. The composite wafer is then diced into individual cameras by sawing and the cameras are then surface mountable to a substrate.

If LEDs and chip-type electronic cameras are surface-mounted on a single flat substrate at the distal end of the endoscope, because LEDs are much thinner than chip-type electronic cameras the cameras may shade portions of a field of view ahead of the distal end of the endoscope.

SUMMARY

In an embodiment, a cavity interposer has a cavity, first bondpads adapted to couple to a chip-type camera cube disposed within a base of the cavity at a first level, the first bondpads coupled through feedthroughs to second bondpads at a base of the interposer at a second level; and third bondpads adapted to couple to a light-emitting diode (LED), the third bondpads at a third level. The third bondpads coupled to fourth bondpads at the base of the interposer at the second level; and the second and fourth bondpads couple to conductors of a cable with the first, second, and third level different. In embodiments, an endoscope optical includes the cavity interposer an LED, and a chip-type camera cube electrically bonded to the first bondpads; the LED is bonded to the third bondpads; and a top of the chip-type camera cube and a top of the LED are at a same level.

BRIEF DESCRIPTION OF THE FIGURES

In the figures, same reference numbers in a first and second figures indicate structures having essentially the same description and function as illustrated in the first and second figures.

DETAILED DESCRIPTION OF THE EMBODIMENTS

Figure 1:
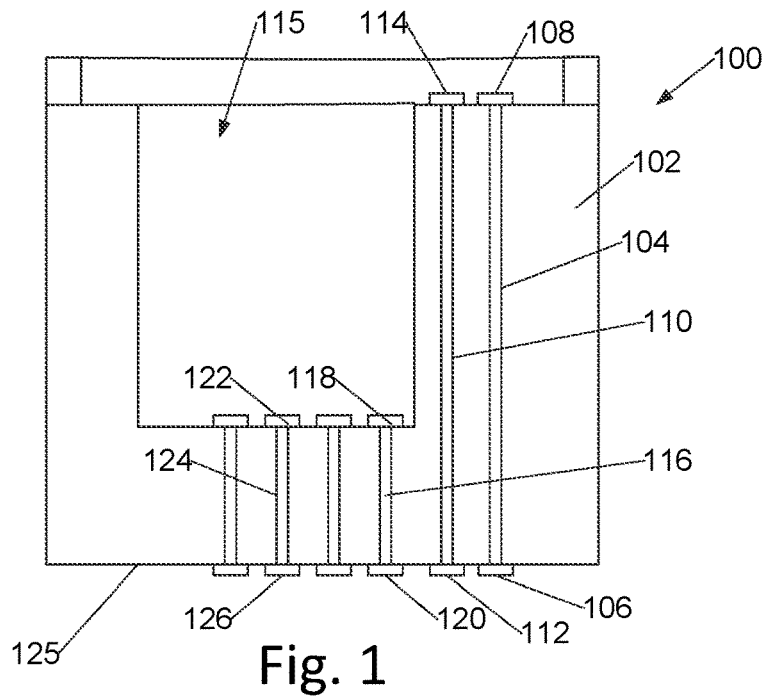
FIG. 1 is a schematic illustration of a cross section of a cavity interposer—a substrate allowing for surface-mounting a camera with lens at a same level as adjacent LED's.

A cavity interposer 100 (FIG. 1) includes a substrate 102 having feedthrough conductors 104, 110 connecting bondpads 108, 114 adapted for ball-bond mounting of light emitting diodes to bondpads 108, 112 adapted to attaching to conductors of a connecting cable. Interposer 100 has a cavity 115 adapted to contain a chip-type "camera cube", having bondpads 118, 122 adapted for ball-bonding to mount a chip-type camera cube (as shown in FIG. 2). Bondpads 118, 122 are coupled through conductive feedthroughs 116, 124 to bondpads 120, 126 at a base 125 of the cavity interposer 100 adapted for attaching individually to conductors of the connecting cable. The cable may have as few as five conductors, although many embodiments, including those with fluorescent stimulus LEDs (see below), may have more than five conductors.

In an embodiment, the cavity interposer 100 is assembled into an endoscope optical head assembly 200 (FIG. 2) with camera cube 202 positioned in cavity 115 with bondpads of camera cube 202 bonded to bondpads 118, 122. Optical head assembly also includes at least one light-emitting diode (LED) 204 bonded to bondpads 108, 114 and configured to illuminate objects within a field of view that can be imaged by camera cube 202, in a particular embodiment LED 204 is a white LED. Optical head assembly 200 also has a transparent protective window 205 sealed with waterproof material and positioned to protect the camera cube 202 and LED 204; to support the transparent protective window 205 above camera cube 202 and LED 204, the cavity interposer may in some embodiments have a rim 216 to support the transparent protective window 205. Camera cube 202 includes an imaging lens 203 and an image sensor 208, together with a spacer (not shown in FIG. 2) that provides sufficient space between imaging lens 203 and image sensor 208 to focus images of objects within the field of view onto the image sensor 208. Typically, image sensor 208 incorporates a color filter array 214 with a tiling pattern of color filters, such as a Bayer-pattern tiling pattern, the color filter array including red, green, and blue bandpass filters to provide full-color images. Camera cube 202 is configured, typically with solder bumps on its lower surface, for bonding to bondpads 118, 122 of cavity interposer 100, and in an embodiment is ball bonded to bondpads 118, 122 of cavity interposer 100. In an alternative embodiment, bondpads of camera cube 202 are electrically bonded to bondpads 118, 122 of cavity interposer 100 with electrically conductive, silver-containing, glue or with an anisotropic conductive film. In the endoscope optical head, bondpads 106, 112, 120, 126, of the lower surface of the cavity interposer 100 are attached to conductors 209 formed on a flexible substrate 210 to form a flexible endoscope cable 212. In an embodiment, a top of camera cube 202 is at the same level as a top of LED 204.

In an embodiment, cavity interposer 100 is a multilayered ceramic structure with cavity 115 formed in one or more layers before the layers are fired together. In an alternative embodiment, cavity interposer 100 is formed of composite materials such as injection-molded plastic or printed-circuitry board material, in this alternative embodiment, holes for feedthroughs 116, 124, 104, 110 may be formed by laser drilling, and the cavity 115 may be formed by mechanical drilling; in an embodiment where cavity interposer is formed of printed-circuit board material, the cavity interposer may be formed of one or more layers of insulating material, two or three layers of conductive material, and one or more layers of insulating support material. Once formed, holes for feedthroughs in some embodiments are plated through to form feedthroughs 116, 124, 104, 110 and in other embodiments feedthroughs 116, 124, 104, 110 are formed by chemical vapor deposition (CVD) or evaporative metal deposition.

In an embodiment, flexible substrate 210 is formed of flexible printed circuit material, and conductors 209 are covered with an insulating material except where bonded at a distal end to bondpads of the cavity interposer and where bonded at a proximal end to additional circuitry.

Figure 2:
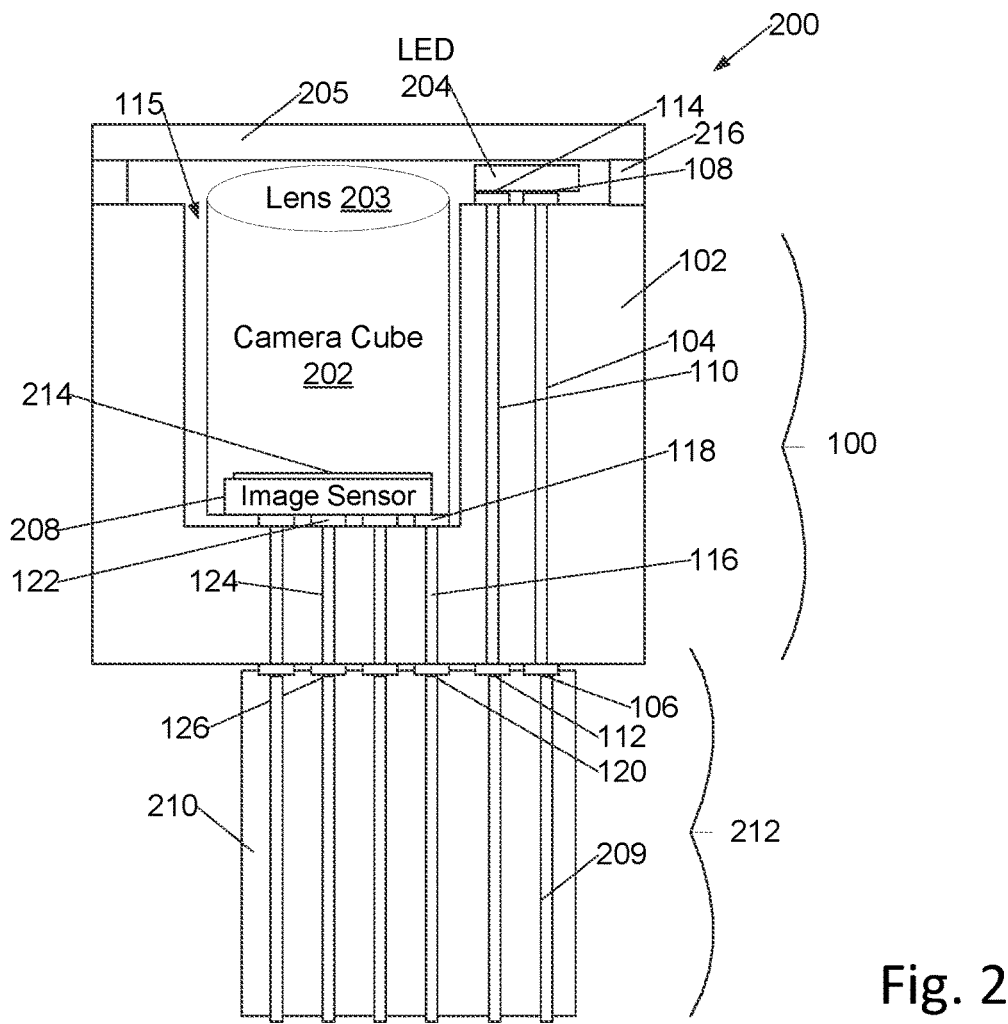
FIG. 2 is a schematic illustration of an optical endoscope head including the cavity interposer of FIG. 1.

In an alternative embodiment, cavity interposer 300 (FIG. 3) is formed such that bondpads 302 associated with the LEDs 304 are not directly under the LEDs (as shown in FIGS. 1 and 2), but are instead adjacent to and at a higher level than a shelf 306 such that an upper surface of LEDs 304 and an upper surface of bondpads 302 are coplanar. With this embodiment, instead of solder-ball bonding LEDs 304, LEDs 304 may be wirebonded to bondpads 302, coupled to bondpads 302 by an anisotropic conductive film 310, or coupled to bondpads 302 by a thin flexible printed circuit. In this embodiment, LED-associated feedthroughs 312 are longer than LED-associated feedthroughs 104 of the embodiment of FIGS. 1 and 2.

Figure 4:
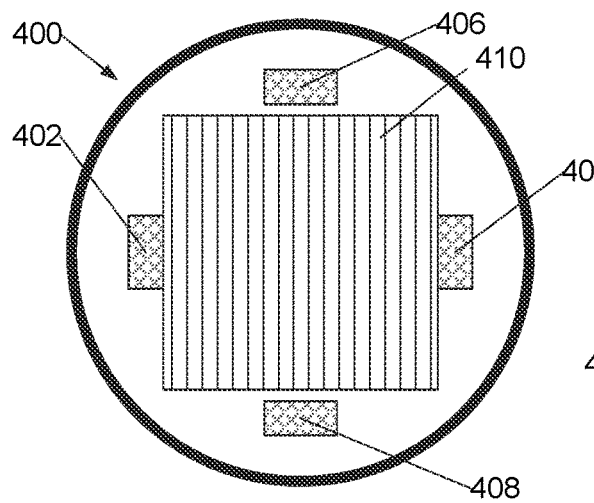
FIG. 4 is a top view of a round optical endoscope head showing mounted LEDs and camera cube.
Figure 5:
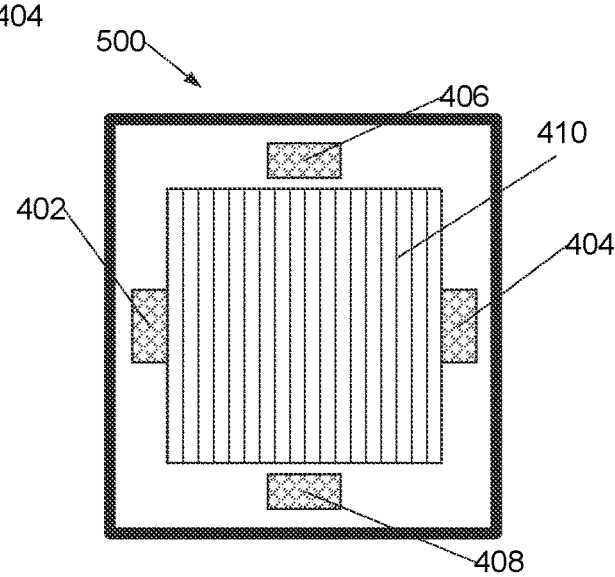
FIG. 5 is a top view of a rectangular optical endoscope head showing mounted LEDs and camera cube.

In a round-interposer 400 (FIG. 4) embodiment there lies beneath window 205 a first LED 402, an optional second LED 404, an optional third LED 406, and an optional fourth LED 408, the LEDs flanking a camera cube 410. In a square-interposer 500 (FIG. 5) embodiment, there also lies beneath window 205 a first LED 402, an optional second LED 404, an optional third LED 406, and an optional fourth LED 408, the LEDs flanking a camera cube 410.

In alternative embodiments, there may be more than one LED, in some embodiments at least one white LED is provided for white-light color imaging and a separate fluorescent-imaging LED is provided and adapted to provide a fluorescent stimulus wavelength, fluorescent-imaging LED may have a filter to block light of wavelengths that pass through fluorescent-imaging tiles of color filter array 214. In embodiments having a fluorescent stimulus or excitation wavelength LED, there may be a fluorescence-stimulus wavelength-blocking filter incorporated into the tiling pattern of the color filter array 214 that is configured to pass light of a fluorescent emissions wavelength of a fluorophore of interest, and the color filter array 214 may be tiled with a color filter tiling patterns including more than the three, red, green, and blue, filters of a traditional Bayer-pattern filter. In particular embodiments, in addition to red, green, and blue filters in each tiling pattern there are color filters having a passband in the near-infrared, and one or more color filters having passbands associated with each of one or more fluorophores. For example, the embodiment of FIG. 5 may be assembled with two white-light LEDs 402, 404 disposed on opposite sides of camera cube 410, and two fluorescence stimulus wavelength LEDs 406, 408. In alternative embodiments, there may be fluorescence stimulus wavelength LEDs of several different wavelengths to allow detection of, and discrimination between, multiple fluorophores in tissue.

The endoscope optical head assembly 200 is used as a component of an endoscope or other device requiring imaging in tight spots such as borescope for performing optical inspections of cylinder bores of engines or interiors of barrels of guns. Medical uses of endoscopes using the optical head assembly include colonoscopes, hysteroscopes, laparoscopes, and sigmoidoscopes as well as laryngoscopes. In particular embodiments, the entire endoscope optical head 400 or 500, including interposer, has an outside diameter of less than one and a half millimeters and is particularly adapted for use in small-diameter endoscopes such as bronchoscopes, falloposcopes, and cystoscopes.

Figure 6:
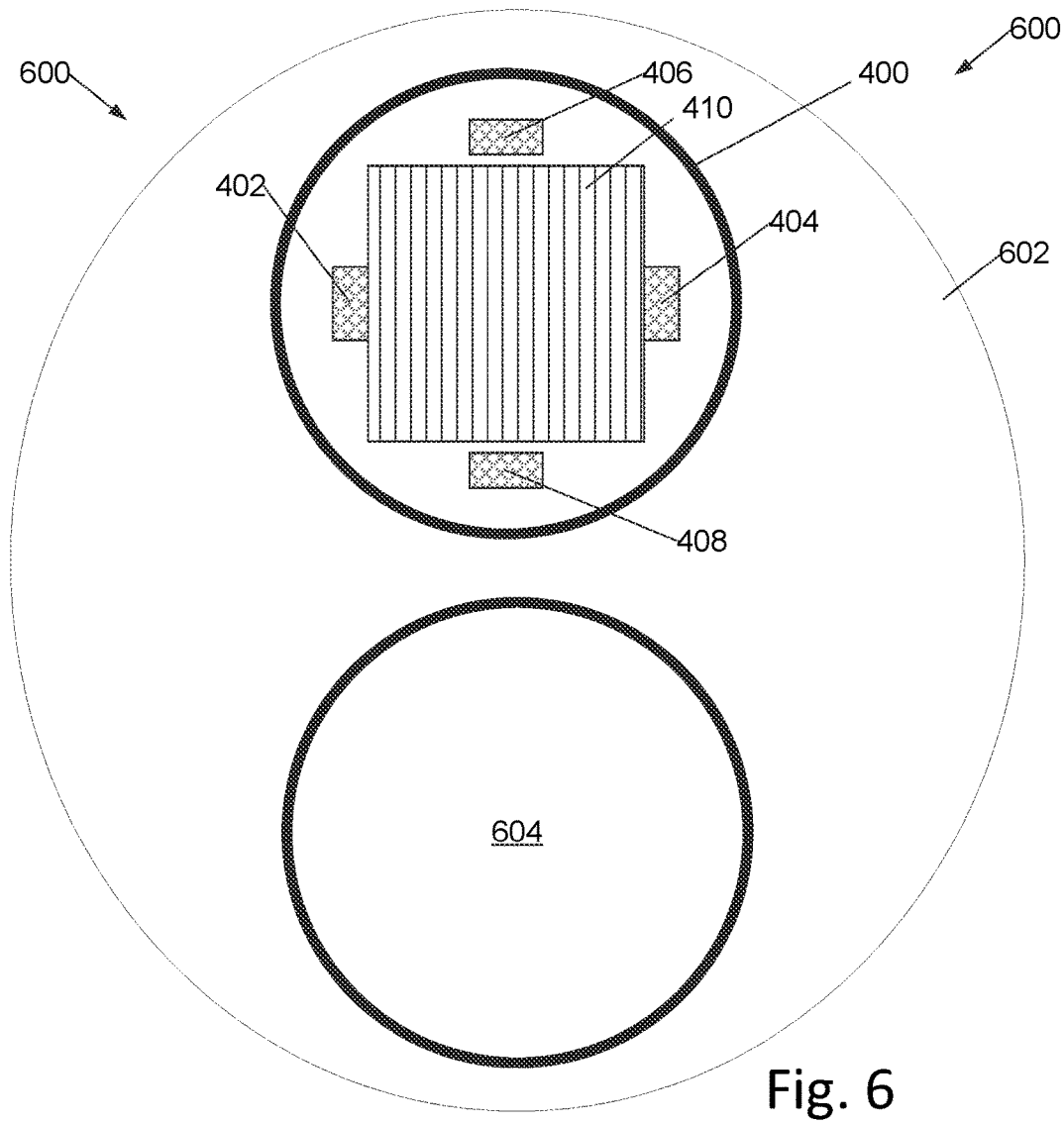
FIG. 6 is an end view of an endoscope incorporating the optical endoscope head of FIG. 4.
Figure 7:
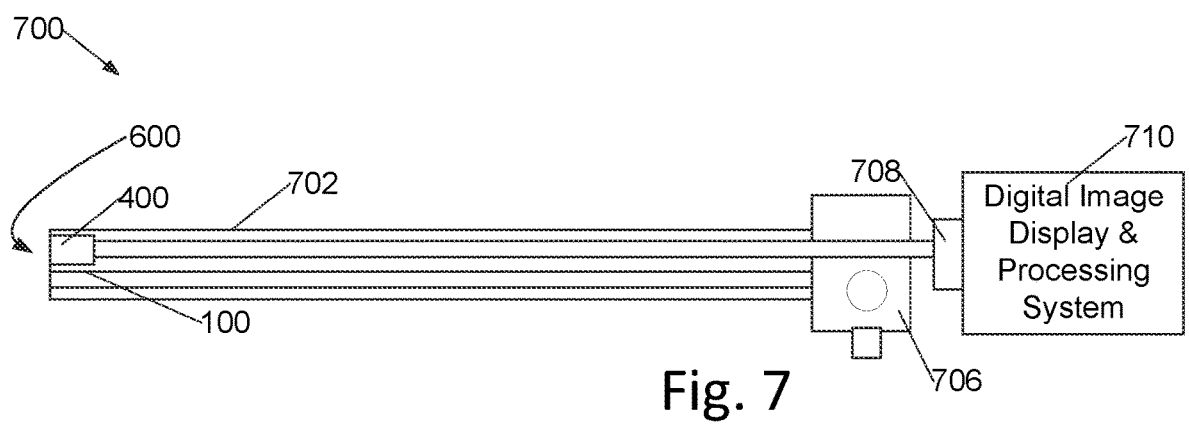
FIG. 7 is a schematic illustration of a cross section of an endoscope incorporating the optical endoscope head of FIG. 2 or FIG. 4.

In a typical endoscopic application, an endoscope end 600 (FIG. 6) includes an end of an endoscope body 602, the endoscope optical head 400, attachment points for one or more steering wires (not shown), and an opening of a lumen 604 through endoscope body 602 through which operative tools such as but not limited to electrocauteries, wire loops, and cell samplers may reach a field of view in front of the endoscope optical head 400. The endoscope end 600 forms an end of endoscope 700 with endoscope body 702, optical endoscope head 400, operating handle 706 that may include controls for steering wires, and a connector 708 to an electronic digital image display & processing system 710 that displays images for guidance to a physician or other user.

Figure 3:
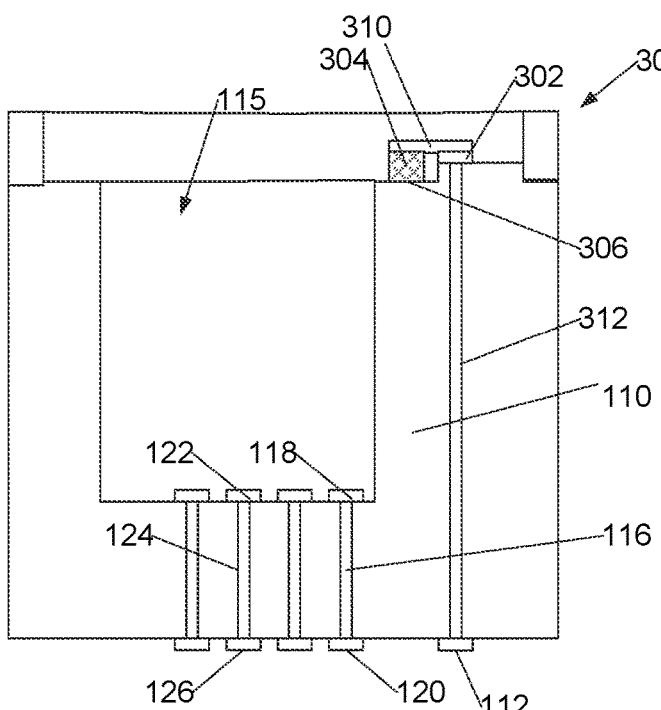
FIG. 3 is a schematic cross section illustration of an alternative embodiment of a cavity interposer showing an attached LED.

In embodiments, the endoscope optical head is formed by fabricating a wafer of cavity interposers, the cavity interposers individually shaped as describe with reference to FIG. 1 or FIG. 3, but not yet diced into individual cavity interposers. Individual diced chip-type cameras are then inserted into, and bonded to bondpads at a first level of, each cavity of the cavity interposers, and LEDs are also attached and bonded to bondpads of a third level of the cavity interposers. Each bondpad of first and third level of the interposers is coupled through feedthroughs to bondpads of the cavity interposers at a second level.

In embodiments lacking rim 216, a spacer wafer may be bonded to the wafer of cavity interposers. A wafer of protective windows is then bonded atop the cavity interposers or atop the spacer wafer. The cavity interposer is then diced, typically by sawing, and conductors of cables are attached to the second level bondpads of the cavity interposers.

Combinations

A cavity interposer designated A has a body configured with a cavity, a plurality of first bondpads adapted to couple to bondpads of a chip-type camera cube (CCube), the first bondpads disposed within a base of the cavity at a first level, the first bondpads coupled through feedthroughs to second bondpads at a base of the cavity interposer at a second level; and a plurality of third bondpads adapted to couple to bondpads of an light-emitting diode (LED), the third bondpads disposed at a third level. The third bondpads coupled through feedthroughs to fourth bondpads at the base of the cavity interposer at the second level; and the second and fourth bondpads are adapted to couple to conductors of a cable with the first, second, and third level different.

An endoscope optical head designated AA includes the cavity interposer designated A, at least one LED, and a chip-type camera cube, where the chip-type camera cube is electrically bonded to the first bondpads; the LED is bonded to the third bondpads; and a top of the chip-type camera cube and a top of the LED are at a same level.

An endoscope optical head designated AB includes the endoscope optical head designated AA and has a cable comprising a plurality of electrical conductors, the plurality of electrical conductors bonded to bondpads of second or fourth bondpads.

An endoscope optical head designated AC includes the endoscope optical head designated AA or AB and has the LED is ball bonded to the third bondpads.

An endoscope optical head designated AD includes the endoscope optical head designated AA or AB and has the LED wire bonded to the third bondpads, and where the third bondpads are at a same level as the top of the LED An endoscope optical head designated AE includes the endoscope optical head designated AA, AB, AC, or AD wherein the camera cube has a tiling pattern including an infrared optical filter.

An endoscope optical head designated AF includes the endoscope optical head designated AA, AB, AC, AD, or AE wherein there are a plurality of LEDs, and at least one LED is a white LED and at least one LED is a fluorescent stimulus wavelength LED.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween. It is also anticipated that steps of methods may be performed in an order different from that illustrated and still be within the meaning of the claims that follow.

What is claimed is:

1. An endoscope optical head comprising:
    a cavity interposer having a body having a top surface, and a bottom surface, the top surface of the body having a depressed portion forming a cavity at the top surface of the body, the body comprising:
    a plurality of first bondpads adapted to couple to bondpads of a chip-type camera cube (CCube), the first bondpads disposed within the cavity and on a base of the cavity at a first level, the first bondpads coupled through feedthroughs to second bondpads on the bottom surface of the cavity interposer at a second level, and
    a plurality of third bondpads adapted to couple to bondpads of at least one light-emitting diode (LED), the third bondpads disposed at a third level on the top surface of the cavity interposer;
    the third bondpads coupled through feedthroughs to fourth bondpads at the base of the cavity interposer at the second level;
    the second and fourth bondpads adapted to couple to conductors of a cable, and
    the first, second, and third level being different;
    at least one LED, and a chip-type camera cube, where:
    the chip-type camera cube is ball-bonded to the first bondpads;
    wherein the chip-type camera cube comprises an imaging lens and an image sensor;
    the at least one LED is bonded to the third bondpads; and
    a top of the chip-type camera cube and a top of the at least one LED are at a same level.

2. An endoscope optical head of claim 1 further comprising:
    a cable comprising a plurality of electrical conductors, the plurality of electrical conductors bonded to bondpads of second or fourth bondpads.

3. The endoscope optical head of claim 2 wherein the at least one LED comprises a first LED ball bonded to the third bondpads.

4. The endoscope optical head of claim 3 wherein the camera cube has a tiling pattern including an infrared optical filter.

5. The endoscope optical head of claim 4 wherein the at least one LED comprises at least one white LED and at least one fluorescent stimulus wavelength LED.

6. The system of claim 4 wherein the at least one LED comprises a second LED coupled to third bondpads of the cavity interposer, the second LED being adapted to provide light at a fluorescent stimulus wavelength, and the chip-type camera cube having a color filter array tiled with a pattern comprising a filter configured to block the light of the fluorescent stimulus wavelength while passing light of a fluorescent emissions wavelength.

7. The endoscope optical head of claim 2 wherein the at least one LED is wire bonded to the third bondpads, and where the third bondpads are at a same level as the top of the LED.

8. The endoscope optical head of claim 7 wherein the camera cube has a tiling pattern including an infrared optical filter.

9. The endoscope optical head of claim 8 wherein the at least one LED comprises at least one white LED and at least one fluorescent stimulus wavelength LED.

10. A method of forming an endoscope with tops of LEDs coplanar with a top of a camera cube comprising:
    bonding a camera cube to first bondpads of a cavity interposer of claim 1, the first bondpads of the cavity interposer being at a first height relative to a bottom of the cavity interposer; and
    bonding at least one light-emitting diode (LED) to third bondpads of the cavity interposer, the third bondpads of the cavity interposer being at a second height relative to the bottom of the cavity interposer, the first height being different than the second height, the third bondpads of the cavity interposer being coupled to fourth bondpads of the cavity interposer, the fourth bondpads of the cavity interposer being on the bottom of the cavity interposer;
    where the first height and second height are chosen so a top of the LED is level with a top of the camera cube.

11. The method of claim 10 further comprising attaching a clear window above a top of the LED and the camera cube.

12. The method of claim 11 further comprising attaching a spacer to the cavity interposer before attaching the clear window above a top of the LED and the camera cube.

13. An endoscopic imaging system including an endoscope comprising:
    a cavity interposer comprising a body having a top surface, and a bottom surface, the top surface having a depressed portion forming a cavity at the top surface, the body comprising:
    a plurality of first bondpads adapted to couple to bondpads of a chip-type camera cube (CCube), the first bondpads disposed within the cavity and on a base of the cavity at a first level, the first bondpads coupled through feedthroughs to second bondpads on the bottom surface of the cavity interposer at a second level, and a plurality of third bondpads adapted to couple to bondpads of at least one light-emitting diode (LED), the third bondpads disposed at a third level on the top surface of the cavity interposer, the third bondpads coupled through feedthroughs to fourth bondpads at the base of the cavity interposer at the second level, the second and fourth bondpads adapted to couple to conductors of a cable, and the first, second, and third level being different;

a chip-type camera cube disposed within the cavity of the cavity interposer and having bondpads electrically coupled to the first bondpads of the cavity interposer;

a light emitting diode mounted to the third bondpads of the cavity interposer;

a cable having a first end coupled to the second and fourth bondpads of the cavity interposer and a second end coupled to a connector; and the connector electrically connected to a digital image display and processing system.

14. An endoscope optical head comprising:

a cavity interposer having a monolithic substrate having a top surface, and a bottom surface, the top surface having a depressed portion forming a cavity at the top surface, the interposer comprising:

a plurality of first bond pads adapted to couple to bond pads of a chip-type camera cube (CCube), the first bondpads disposed within the cavity and on a base of the cavity at a first level, the first bondpads coupled through feedthroughs to second bond pads on the bottom surface of the substrate at a second level, and a plurality of third bondpads adapted to couple to bondpads of at least one light emitting diode (LED), the third bond pads disposed at a third level on the top surface of the substrate and coupled through feedthroughs to fourth bondpads on the bottom surface of the substrate at the second level, the first, second, and third level being different, at least one LED bonded to the third bondpads;

the second and fourth bondpads adapted to couple to conductors of a cable;

at least one LED, and a chip-type camera cube, where:

the chip-type camera cube is ball-bonded to the first bondpads;

the at least one LED is bonded to the third bondpads; and a top of the chip-type camera cube and a top of the at least one LED are at a same level;

the chip-type camera cube further comprising an imaging lens and an image sensor.

15. An endoscope optical head of claim 14 further comprising:

a cable comprising a plurality of electrical conductors, the plurality of electrical conductors bonded to bondpads of second or fourth bondpads.

16. The endoscope optical head of claim 14 wherein the at least one LED is ball bonded to the third bondpads.

17. The endoscope optical head of claim 14 wherein the at least one LED is wire bonded to the third bondpads, and where the third bondpads are at a same level as the top of the LED.

18. The endoscope optical head of claim 14 wherein the camera cube has a tiling pattern including an infrared optical filter.

* * * * *